(12) United States Patent
Chu et al.

(10) Patent No.: US 7,863,406 B2
(45) Date of Patent: Jan. 4, 2011

(54) UNSATURATED POLY(ESTER-AMIDE) BIOMATERIALS

(75) Inventors: Chih-Chang Chu, Ithaca, NY (US); Ramaz Katsarava, Tbilisi (GE); Kai Guo, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 372 days.

(21) Appl. No.: 11/587,530

(22) PCT Filed: May 31, 2005

(86) PCT No.: PCT/US2005/019088

§ 371 (c)(1), (2), (4) Date: Oct. 25, 2006

(87) PCT Pub. No.: WO2005/121250

PCT Pub. Date: Dec. 22, 2005

(65) Prior Publication Data

US 2007/0167605 A1 Jul. 19, 2007

Related U.S. Application Data

(60) Provisional application No. 60/576,293, filed on Jun. 3, 2004, provisional application No. 60/638,385, filed on Dec. 27, 2004.

(51) Int. Cl.
  *C08G 69/10* (2006.01)
  *C08G 69/44* (2006.01)
  *C08L 77/04* (2006.01)
  *C08L 77/12* (2006.01)

(52) U.S. Cl. .................. 528/272; 528/303; 528/306; 528/328; 528/345; 528/392; 525/54.1; 525/54.2; 525/421; 525/434; 525/436; 525/437; 525/447; 424/497

(58) Field of Classification Search .................. 528/288, 528/310, 328, 272, 300; 525/421, 420, 426
See application file for complete search history.

(56) References Cited

U.S. PATENT DOCUMENTS

| 4,115,370 | A | * | 9/1978 | Corrado ................. 525/420.5 |
| 4,180,646 | A | * | 12/1979 | Choi et al. ................. 528/153 |
| 4,999,417 | A | * | 3/1991 | Domb ................. 528/271 |
| 5,278,201 | A | | 1/1994 | Dunn et al. |
| 5,610,241 | A | | 3/1997 | Lee et al. |
| 5,707,647 | A | | 1/1998 | Dunn et al. |
| 5,919,893 | A | | 7/1999 | Roby et al. |
| 6,503,538 | B1 | | 1/2003 | Chu et al. |
| 2003/0175408 | A1 | * | 9/2003 | Timm et al. ................. 427/2.1 |

FOREIGN PATENT DOCUMENTS

WO   WO 03/062298   7/2003

OTHER PUBLICATIONS

Guo, K., et al., "Synthesis and Characterization of Novel Biodegradable Unsaturated Poly(ester amide)s", J. of Poly. Sci.: Part A: Poly. Chem. vol. 43, 1463-1477 (2005).
Katsarava, R., et al., "Amino Acid-Based Bioanalogous Polymers. Synthesis, and Study of Regular Poly(ester amide)s Based on Bis(α-amino acid) α,ω-Alkene Diesters, and Aliphatic Dicarboxylic Acids", J. of Poly. Sci.: Part A: Poly. Chem., vol. 37, 391-407 (1999).

* cited by examiner

*Primary Examiner*—Randy Gulakowski
*Assistant Examiner*—Rachel Kahn
(74) *Attorney, Agent, or Firm*—Hodgson Russ LLP

(57) ABSTRACT

Biodegradable poly(ester-amides) are synthesized from amino acids, diols and dicarboxylic acids where one or both of the diols and dicarboxylic acids contain unsaturation; e.g., from di-p-nitrophenyl dicarboxylates and p-toluenesulfonic acid salts of bis(alpha-amino acid) disesters of diols where one or both of the dicarboxylate and diol moieties contain unsaturation or from di-p-nitrophenyl dicarboxylates, and p-toluene-sulfonic acid salts of bis(alpha-amino acid) diesters of diols and p-toluenesulfonic acid salt of lysine ester where one or both of the dicarboxylate and diol moieties contain unsaturation. The polymers are useful as biodegradable carriers for drugs of other bioactive agents.

2 Claims, No Drawings

UNSATURATED POLY(ESTER-AMIDE) BIOMATERIALS

CROSS-REFERENCE TO RELATED APPLICATIONS

This application is a 371 national phase of PCT Application No. PCT/US2005/019088, filed May 31, 2005, which claims the benefit of U.S. Provisional Patent Application No. 60/576,293, filed Jun. 3, 2004 and of U.S. Provisional Patent Application No. 60/638,385 filed Dec. 27, 2004, the whole of both of which are Incorporated herein by reference.

The invention was made at least in part with United States Government support under United States Department of Commerce Prime Grant Award No. 99-27-07400 pursuant to a subagreement with The National Textile Center. The United States Government has certain rights in the invention.

TECHNICAL FIELD

This invention is directed at poly(ester-amide) biomaterials useful as biodegradable carriers for drugs or other bioactive agents.

BACKGROUND OF THE INVENTION

Poly(ester-amide)s (PEAs) are polymers synthesized from non-toxic amino acids, diols and dicarboxylic acids and are composed of both ester and amide blocks. They have been widely studied because they combine the favorable properties of both polyesters and polyamides, i.e., they possess not only good biodegradability but also good mechanical and processing properties, e.g., thermal stability, tensile strength and modulus. Amino acids, due to their abundant availability from natural sources and the potential biodegradability of their derivatives under certain enzymatic catalyzed conditions, have often been chosen as the source for the amine group of the biodegradable poly(ester-amide)s. It has also been reported that the inclusion of phenylalanine in the backbone of the PEAs can enhance their biodegradability in the presence of chymotrypsin.

All PEAs reported in the literature contain saturated backbone bridging structures. See, for example, U.S. Pat. No. 6,503,538 B1. This means that the PEAs synthesized before now, have to be modified before other chemicals can be reacted with them.

SUMMARY OF THE INVENTION

In the invention herein, PEAs are provided which have built-in functional groups on PEA backbones, and these built-in functional groups can react with other chemicals and lead to the incorporation of additional functional groups to expand the functionality of PEA further and are therefore ready for reaction with other chemicals including hydrophilic moieties (to increase water solubility), drugs and other bioactive agents, without the necessity of modification first.

In one embodiment the invention is directed at a polymer having the structural formula:

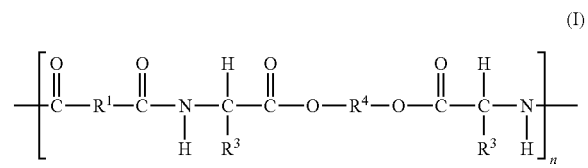

(I)

wherein $R^1$ is selected from the group consisting of $(C_2\text{-}C_{20})$ alkylene and $(C_2\text{-}C_{20})$ alkenylene; $R^3$ is selected from the group consisting of hydrogen, $(C_1\text{-}C_6)$ alkyl, $(C_2\text{-}C_6)$ alkenyl, $(C_2\text{-}C_6)$ alkynyl and $(C_6\text{-}C_{10})$ aryl$(C_1\text{-}C_6)$ alkyl; and $R^4$ is selected from the group consisting of $(C_2\text{-}C_{20})$ alkylene, $(C_2\text{-}C_{20})$ alkenylene, and $((CH_2)_rO)_q$—$(C_2\text{-}C_{20})$ alkylene where r is 2 or 3 and q ranges from 1 to 4, where at least one of $R^1$ and $R^4$ comprises a radical selected from the group consisting of $(C_2\text{-}C_{20})$ alkenylene; and n ranges from about 5 to about 150, e.g., from about 50 to 150.

In one alternative, $R^3$ is $CH_2Ph$ and the amino acid used in synthesis is L-phenylalanine.

In a second embodiment the invention is directed at a polymer having the structural formula:

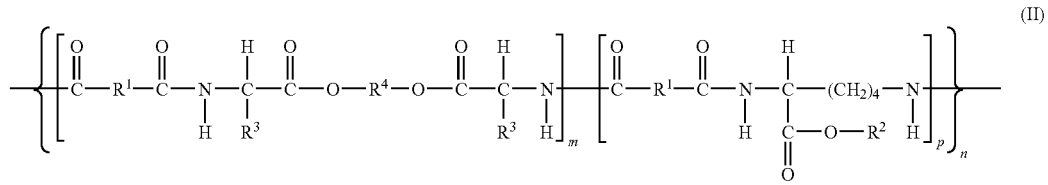

(II)

where m ranges from about 0.1 to about 0.9; p ranges from about 0.9 to about 0.1; n ranges from about 5 to about 150, e.g., about 50 to about 150, each $R^1$ is independently selected from the group consisting of $(C_2\text{-}C_{20}$ alkylene) and $(C_2\text{-}C_{20})$ alkenylene. $R^2$ is hydrogen or $(C_6\text{-}C_{10})$aryl $(C_1\text{-}C_6)$ alkyl or t-butyl or other protecting group; $R^3$ is selected from the group consisting of hydrogen, $(C_1\text{-}C_6)$ alkyl, $(C_2\text{-}C_6)$ alkenyl, $(C_2\text{-}C_6)$ alkynyl and $(C_6\text{-}C_{10})$ aryl $(C_1\text{-}C_6)$ alkyl; and $R^4$ is selected from the group consisting of $(C_2\text{-}C_{20})$ alkylene, $(C_2\text{-}C_{20})$ alkenylene, and $((CH_2)_rO)_q$—$(C_2\text{-}C_{20})$ alkylene where r is 2 or 3 and q ranges from 1 to 4, where one $R^1$ and $R^4$ or both $R^1$s and $R^4$ or both $R^1$s but not $R^4$ or one $R^1$ and not $R^4$ or $R^1$ but no $R^1$s, comprise a radical selected from the group consisting of $(C_2\text{-}C_{20})$ alkenylene.

The term "alkylene" is used herein as a linear saturated divalent to hydrocarbon radical.

The term "alkenylene" is used herein to mean a divalent branched or unbranched hydrocarbon chain containing at least one double bond in the main chain or in a side chain.

The molecular weights and polydisperities herein are determined by gel permeation chromatography using polystyrene standards. More particularly, number and weight average molecular weights ($M_n$ and $M_w$) are determined using a Model 510 gel permeation chromatograph (Water Associates, Inc., Milford, Mass.) equipped with a high-pressure liquid chromatographic pump, a Waters 486 UV detector and a Waters 2410 differential refractive index detector. Tetrahydrofuran (THF) is used as the eluant (1.0 mL/min). The polystyrene standards have a narrow molecular weight distribution.

The polymers herein are denoted UPEAs (unsaturated poly(ester-amide)s).

The term "biodegradable" is used herein to mean capable of being broken down by various enzymes such as trypsins, lipases and lysosomes in the normal functioning of the human body and living organisms (e.g., bacteria) and/or water environment.

The term "biomaterial" is used herein to mean a synthetic material used to function in intimate contact with living tissue.

The term "bioactive agent" is used herein to mean agent for delivery to cells, tissues or organs for nutrient or therapeutic effects. These include, but are not limited to nutrients, pharmaceuticals, drugs, peptides and oligo nucleotides.

The term "about" as used herein is meant to encompass variations of +/−2%, e.g., +/−0.5% or +/−0.1%.

DETAILED DESCRIPTION

We turn now to the UPEAs of the structure (I) as described above.

The polymers of the working examples, are those of the structure (I) where

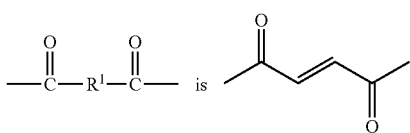

(a)

and/or (b) $R^4$ is —$CH_2$—$CH$=$CH$—$CH_2$—. In the working examples, in cases where (a) is present and (b) is not present, $R^4$ in (I) is —$C_4H_8$— or —$C_6H_{12}$—. In the working examples, in cases where (a) is not present and (b) is present, $R^1$ in (I) is —$C_4H_8$— or —$C_8H_{16}$—.

The UPEAs can be prepared by solution polycondensation of either (1) di-p-toluenesulfonic acid salts of bis(alpha-amino acid) diesters of unsaturated diol and di-p-nitrophenyl ester of saturated dicarboxylic acid or (2) di-p-toluenesulfonic acid salts of bis(alpha-amino acid) diesters of saturated diol and di-nitrophenyl ester of unsaturated dicarboxylic acid or (3) di-p-toluenesulfonic acid salt of bis(alpha-amino acid) diesters of unsaturated diol and di-nitrophenyl ester of unsaturated dicarboxylic acid.

Salts of p-toluenesulfonic acid are known for use in synthesizing polymers containing amino acid residues. The aryl sulfonic acid salts are used instead of the free base because the aryl sulfonic acid salts of bis(alpha-amino acid) diesters are easily purified through recrystallization and render the amino groups as unreactive ammonium tosylates throughout workup.

The di-p-nitrophenyl esters of unsaturated dicarboxylic acid can be synthesized from p-nitrophenol and unsaturated dicarboxylic acid chloride, e.g., by dissolving triethylamine and p-nitrophenol in acetone and adding unsaturated dicarboxylic acid chloride dropwise with stirring at −78° C. and pouring into water to precipitate product. Suitable acid chlorides are dicarboxylic acyl chlorides including, for example, fumaric, maleic, mesaconic, citraconic, glutaconic, itaconic, ethenyl-butane dioic and 2-propenyl-butanedioic acid chlorides.

The di-p-toluenesulfonic acid salts of bis(alpha-amino acid) diesters of unsaturated diol can be prepared by admixing amino acid, aryl sulfonic acid (e.g., p-toluenesulfonic acid monohydrate) and unsaturated diol in toluene, heating to reflux temperature, until water evolution is minimal, then cooling. The unsaturated diols include, for example, 2-butene-1,4-diol and 1,18-octadec-9-en-diol.

Di-p-nitrophenyl esters of saturated dicarboxylic acid and di-p-toluenesulfonic acid salts of bis(alpha-amino acid) diesters of saturated diol can be prepared as described in U.S. Pat. No. 6,503,538 B1.

The first embodiment of the invention is supported by experiments and results and conclusions set forth in Guo, K., et al., Journal of Polymer Science, Part A: Polymer Chemistry 43(7), 1463-1477 (Feb. 15, 2005), the whole of which is incorporated herein by reference.

We turn now to the second embodiment of the invention herein.

The compounds (II) can be made in similar fashion to the compound (VII) of U.S. Pat. No. 6,503,538 except that $R_4$ of (III) of U.S. Pat. No. 6,503,538 and/or $R_1$ of (V) of U.S. Pat. No. 6,503,538 is $C_2$-$C_{20}$ alkenylene as described above. The reaction is carried out, for example, by adding dry triethylamine to a mixture of (III) and (IV) of U.S. Pat. No. 6,503,538 and (V) where at least one of (III) and (V) contains $C_2$-$C_{20}$ alkenylene in dry N,N-dimethylacetamide, at room temperature, then increasing the temperature to 80° C. and stirring for 16 hours, then cooling the reaction solution to room temperature, diluting with ethanol, pouring into water, separating polymer, washing separated polymer with water, drying to about 30C under reduced pressure and then purifying up to negative test on p-nitrophenol and p-toluenesulfonate. A preferred reactant (IV) is p-toluenesulfonic acid salt of L-lysine benzyl ester. When the reactant (IV) is p-toluenesulfonic acid salt of benzyl ester, the benzyl ester protecting group is preferably removed from (II) to confer biodegradability, but it should not be removed by hydrogenolysis as in Example 22 of U.S. Pat. No. 6,503,538 because hydrogenolysis would saturate the desired double bonds; rather the benzyl ester group should be converted to an acid group by a method which would preserve unsaturation, e.g., by treatment with fluoroacetic acid or gaseous HF. Alternatively, the lysine reactant (IV) can be protected by protecting group different from benzyl which can be readily removed in the finished product while preserving unsaturation, e.g., the lysine reactant can be protected with t-butyl (i.e., the reactant can be t-butyl ester of lysine) and the t-butyl can be converted to H while preserving unsaturation by treatment of the product (II) with dilute acid.

For the cases where $R^4$ is $((CH_2)_rO)_q$—$(C_2$-$C_{20})$ alkylene, di-p-toluenesulfonic acid salt of bis(alpha-amino acid) diester of lower oligomer of ethylene glycol is used in place of di-p-toluenesulfonic acid salt of bi(alpha-amino acid) diester of saturated diol and can be prepared by substituting lower oligomer of ethylene glycol (e.g., diethylene glycol, triethylene glycol, tetraethylene glycol or pentaethylene glycol) in place of diol in the synthesis of III described in U.S. Pat. No. 6,503,538 B1.

For both embodiments the following hold:

Aminoxyl radical, e.g., 4-amino TEMPO can be attached using carbonyldiimidazol or suitable carbodiimide as a condensing agent.

Drugs or other bioactive agents, e.g., anti-inflammatory agent (e.g., sirolimus) or antiproliferative drugs (e.g., paclitaxel), or biologic, or protein or cytokine, or oligonucleotide including antisense oligonucleotide, or gene, or carbohydrate, or hormone can be attached via the double bond functionality.

Hydrophilicity can be imparted by bonding to poly(ethylene glycol) diacrylate.

Applications for the polymers of the invention include the following:

1. Copolymerization with other functional monomers or polymer precursors (e.g., for pH-sensitive or temperature sensitive blocks) to provide controllable biodegradability.

2. To conjugate biologically active compounds via the unsaturated double bond(s) of a UPEA so the resulting UPEA has biological activity.

3. Formation of UPEA-based hydrogels via crosslinking of unsaturated double bonds of UPEA.
4. Providing drug carriers, e.g., via application 2 above or by inclusion in hydrogel of application 3 above.
5. Substrates for tissue engineering.

The invention is illustrated by the following working examples:

WORKING EXAMPLE I

In this example, the synthesis and characterization of a series of biodegradable UPEAs of the first embodiment of the invention by the solution polycondensation of two unsaturated monomers, di-p-nitrophenyl fumarate (NF) and p-toluenesulfonic acid salt of bis(L-phenylalanine)2-butene-1,4-diester (PBe), and four saturated monomers, namely p-toluenesulfonic acid salt of bis(L-phenylalanine) butane-1,4-diester (PB), p-toluenesulfonic acid salt of bis(L-phenylalanine) hexane-1,6-diester (PH), di-p-nitrophenyl adipate (NA), and di-p-nitrophenyl sebacate (NS), are described. The effects of reaction time, temperature, and different solvents on the molecular weights and molecular weight distributions (MWDs) of the resultant polymers are considered.

NA and NS were prepared through the reaction of the corresponding dicarboxylic acyl chlorides with p-nitrophenol as described in Katsarava, R., et al., J. Polym. Sci., Part A: Polym. Chem. 37, 391-407 (1999).

NF was synthesized from p-nitrophenol and fumaryl chloride (FC) according to a modification of conditions used for synthesis of NA and NS, as follows: A solution of triethylamine (0.0603 mol) and p-nitrophenol (0.0603 mol) in 100 mL of acetone was prepared at room temperature, and this solution was kept at −78° C. with dry ice and acetone. FC (0.03 mol, 3.2 mL) in 40 mL of acetone was then added to the chilled solution dropwise with stirring for 2 h at −78° C. and then with stirring at room temperature overnight. After that, the mixture was poured into 800 mL of distilled water to precipitate the product, NF, which was filtered, washed thoroughly with distilled water, dried in vacuo at 50° C., and finally purified by recrystallization from acetonitrile three times.

(PBe), (PB) and (PH) were prepared as follows: L-Phenylalanine (0.132 mol), p-toluenesulfonic acid monohydrate (0.132 mol), and diol (0.06 mol) in 250 mL of toluene were placed in a flask equipped with a Dean-Stark apparatus, a $CaCl_2$ drying tube, and a magnetic stirrer. The solid-liquid reaction mixture was heated to reflux for 16 h until 4.3 mL (0.24 mol) of water evolved. The reaction mixture was then cooled to room temperature, filtered and dried in vacuo, and finally purified by recrystallization three times. According to the type of di-p-toluenesulfonic acid salt of bis(L-phenylalanine) diester synthesized, different solvents were used for recrystallization. For example, water and n-butanol were used as recrystallization media for the di-p-toluenesulfonic acid salt of bis(L-phenylalanine) butane-1,4-diester (PB) and di-p-toluenesulfonic acid salt of bis (L-phenylalanine) 2-butene-1,4-diester (PBe), respectively. Water was used as the recrystallization medium for (PH).

Five different UPEAs were prepared, two by solution polycondensation of NF with PB and NF with PH and two by solution polymerization of PBe with NA and PBe with NS and one by solution polymerization of NF and PBe. The combinations used are set forth in Table 1 below:

TABLE 1

| Monomer Combination | Monomer Containing C=C | Obtained Polymer |
| --- | --- | --- |
| NF + PB | NF | FPB |
| NF + PH | NF | FPH |
| NF + PBe | NF and PBe | FPBe |

TABLE 1-continued

| Monomer Combination | Monomer Containing C=C | Obtained Polymer |
| --- | --- | --- |
| NS + PBe | PBe | SPBe |
| NA + PBe | PBe | APBe |

In the solution polycondensations, excess triethylamine was used as the acid receptor for p-toluenesulfonic acid during the polymerization to regenerate free amino groups in the di-p-toluenesulfonic acid salt monomer. Polymerization took place in a homogeneous phase, and the polymer obtained remained dissolved in the reaction solution, except that the reaction solution of FPH became a gel-like mixture after a certain time (longer at room temperature and shorter at a high temperature). The gel-like mixture that formed during FPH synthesis was proved to be not a real gel because it could dissolve in hexafluoroisopropanol and m-cresol, the latter being used as the solvent for viscosity measurements.

An example of the synthesis of APBe via solution polycondensation is given to illustrate the details of the synthesis procedures. Triethylamine (0.31 mL, 2.2 mmol) was added dropwise to a mixture of monomers NA (1.0 mmol) and PBe (1.0 mmol) in 1.5 mL of dry DMA, and the solution was heated to 60° C. with stirring until the complete dissolution of the monomers. The reaction vial was then kept under a specified temperature (25° C. or 70° C.) for predetermined durations (24, 48, 72, or 96 h) without stirring to determine the effects of the temperature and reaction duration on the polymerization reaction. The resulting solution was precipitated with cold ethyl acetate, filtered, extracted by ethyl acetate in a Soxhlet apparatus for 48 h, and finally dried in vacuo at 50° C.

Confirmation that APBe was formed having the structure

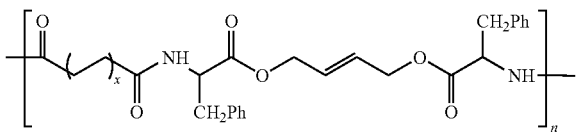

where x=2, was confirmed by FTIR and NMR spectral data.

The effects of type of solvent, reaction temperature and reaction solvent, on reduced viscosity and molecular weight of UPEAs were examined.

We turn now to the effect of different solvents on SPBe and FPB products formed. Three organic solvents were used, namely N-methyl pyrrolidone (NMP), N,N-dimethylformamide (DMF) and N,N-dimethylacetamide (DMA). In all three solvents, the reaction proceeded homogeneously. FPB would not dissolve in tetrahydrofuran (THF) or other normal organic solvents for molecular weight and MWD measurements so no data was observed for these for FPB. The results are set forth in Table 2 below:

TABLE 2

| | | Reduced Viscosity | Molecular Weight (kg/mol) | | |
| --- | --- | --- | --- | --- | --- |
| Sample | Solvent | (dL/g) | $M_n$ | $M_w$ | $M_w/M_n$ |
| SPBe1 | NMP | 0.37 | 10.7 | 16.4 | 1.54 |
| SPBe2 | DMF | 0.48 | 17.5 | 25.1 | 1.43 |
| SPBe3 | DMA | 0.46 | 17.3 | 24.7 | 1.43 |
| FPB1 | NMP | 0.36 | — | — | — |
| FPB2 | DMF | 0.43 | — | — | — |
| FPB3 | DMA | 0.47 | — | — | — |

All the reaction were carried out at 70° C. for 48 h. The concentration of the reaction solution was 1.10 mol/L.

As shown in Table 2, SPBe obtained in DMF and SPBe obtained in DMA had a similar molecular weight and reduced viscosity value, which were much higher than those of SPBe synthesized in NMP. SPBe prepared in NMP also had a wider MWD than those prepared in DMF and DMA. FPB obtained in DMA had the highest reduced viscosity value of the FPB polymers synthesized in DMA, NMP and DMF. NMP was consequently not a good solvent for preparing high molecular weight UPEAs. When DMF was used as the solvent for FPB synthesis, the reaction solution became a gel-like mixture. This restricted chain propagation during polycondensation and led to the formation of polymers of relatively lower molecular weights. Such a less desirable reaction condition was improved when DMA was used as the solvent. Therefore, DMA was found to be the best solvent for the SPBe and FPB synthesis.

The effects of reaction temperature (25° C. or 70° C.) and reaction times (24, 48, 72, 96 h) determined at those temperatures on the molecular weight and reduced viscosity of SPBe products were determined. Results are set forth in Table 3 below:

TABLE 3

| | 25° C. | | | | 70° C. | | | |
|---|---|---|---|---|---|---|---|---|
| Reaction Time (h) | Reduced Viscosity (dL/g) | $M_n$ (kg/mol) | $M_w$ (kg/mol) | $M_w/M_n$ | Reduced Viscosity (dL/g) | $M_n$ (kg/mol) | $M_w$ (kg/mol) | $M_w/M_n$ |
| 24 | 0.37 | 14.0 | 22.6 | 1.61 | 0.50 | 17.5 | 25.5 | 1.45 |
| 48 | 0.44 | 13.4 | 21.5 | 1.60 | 0.46 | 17.3 | 24.7 | 1.43 |
| 72 | 0.45 | 15.1 | 25.5 | 1.68 | 0.39 | 14.1 | 19.5 | 1.38 |
| 96 | 0.57 | 16.8 | 28.5 | 1.70 | 0.56 | 20.5 | 29.7 | 1.45 |

As shown in Table 3, $M_n$, $M_w$ and reduced viscosity of SPBe increased with reaction duration, whereas MWD had a relatively smaller increase. A higher reaction temperature (70° C.) increased not only the polymerization rate but also the molecular weights ($M_n$ and $M_w$) and not at the expense of the MWD. The MWDs of the polymer obtained at 70° C. (average 1.4) appeared to become narrower than that of the polymerization conducted at room temperature (average 1.6) and were less dependent on the reaction time. The molecular weights at 70° C. did not increase with the reaction time as much as those at 25° C.

On the basis of these data, the polycondensation of UPEA was subsequently optimized to be carried out in DMA at 70° C. for 48 h (for a reaction as complete as possible), unless otherwise specified.

Elemental analysis results are set forth in Table 4 below:

TABLE 4

| Sample | Formula | Empirical Formula (g/mol) | Calculated (%) | | | Experimental (%) | | |
|---|---|---|---|---|---|---|---|---|
| | | | C | H | N | C | H | N |
| FPB | $(C_{26}H_{28}N_2O_6)_n$ | 464.52n | 67.23 | 6.08 | 6.03 | 66.69 | 6.00 | 6.03 |
| FPH | $(C_{28}H_{32}N_2O_6)_n$ | 492.57n | 68.28 | 6.55 | 5.69 | 67.02 | 6.43 | 5.56 |
| FPBe | $(C_{26}H_{26}N_2O_6)_n$ | 462.50n | 67.52 | 5.67 | 6.06 | 65.86 | 5.62 | 5.92 |
| APBe | $(C_{28}H_{32}N_2O_6)_n$ | 492.57n | 68.28 | 6.55 | 5.69 | 66.85 | 6.65 | 5.68 |
| SPBe | $(C_{32}H_{40}N_2O_6)_n$ | 548.68n | 70.05 | 7.35 | 5.10 | 69.05 | 7.27 | 5.02 |

Fundamental properties of the synthesized UPEAs were determined and are set forth in Table 5 below:

TABLE 5

| | Empirical Formula (FW) | Yield (%) | Reduced Viscosity (dL/g)[b] | $M_n$ (kg/mol) | $M_w$ (kg/mol) | $M_w/M_n$ | $T_g$ (° C.) | $T_m$ (° C.) |
|---|---|---|---|---|---|---|---|---|
| FPB | $C_{26}H_{28}N_2O_6)_n$ [(464.53)$_n$] | 86 | 0.43 | — | — | — | 103 | ~250 |
| FPH | $C_{28}H_{32}N_2O_6)_n$ [(492.57)$_n$] | 87 | 0.30 | — | — | — | 92 | ~216 |
| FPBe | $C_{26}H_{26}N_2O_6)_n$ [(462.50)$_n$] | 74 | 0.35 | — | — | — | 109 | ~223 |

TABLE 5-continued

| | Empirical Formula (FW) | Yield (%) | Reduced Viscosity (dL/g)[b] | $M_n$ (kg/mol) | $M_w$ (kg/mol) | $M_w/M_n$ | $T_g$ (° C.) | $T_m$ (° C.) |
|---|---|---|---|---|---|---|---|---|
| APBe | $C_{28}H_{32}N_2O_6)_n$ [(492.57)$_n$] | 84 | 0.25 | 15.6 | 22.8 | 1.46 | 61 | N/A[c] |
| SPBe | $C_{32}H_{40}N_2O_6)_n$ [(548.68)$_n$] | 54 | 0.46 | 17.3 | 24.7 | 1.43 | 46 | N/A[c] |

[a]Synthesis conditions: concentration 10 mol/L, temperature 70° C., DMA solvent.
[b]Measured in m-cresol at 25° C. (concentration 0.25 g/dl).
[c]Polymer decomposed when the temperature was greater than 240° C.

The UPEAs had higher $T_g$ than the corresponding saturated PEAs. This was because these UPEAs had one or two C═C double bonds in every repeating unit of the molecules. Such a structure reduced the flexibility of the polymer molecules and increased the difficulty of chain-segment movement (i.e., higher $T_g$).

For all five UPEAs, the location of the C═C double bond in the polymer backbone had a profound effect on $T_g$. FPBe, which had the C═C double bond in both the diester and diamide parts and thus the highest polymer chain rigidity, had the highest $T_g$ (109° C.). The UPEAs based only on fumaryl, FPB and FPH, had the C═C double bond in the diamide part; the C═C double bonds also conjugated with the two carbonyl groups and resulted in a higher ridigidity of the polymer backbone. The butenyl-based UPEAs, APBe and SPBe, had isolated C═C double bonds in the diester part only; also, the 2-butene-1,4-diol used in the monomer synthesis for APBe and SPBe was a cis/trans mixture, which created some free volume that counteracted some of the rigid effect brought by C═C double bonds on the polymer molecules. Therefore, APBe and SPBe had much lower $T_g$'s than FPB and FPH.

On the other hand, the effect of the length of the methylene groups in the repeating unit of UPEAs on $T_g$ can best be illustrated by a comparison of the $T_g$ data for APBe and SPBe or for FPB and FPH. Such a comparison of $T_g$ data indicated that those UPEAs with longer —$CH_2$— chain segments in their repeating units, such as SPBe and FPH, had lower $T_g$'s and the $T_g$ of SPBe was the lowest of all five UPEAs. This relationship between $T_g$ and the number of methylene groups in UPEA can be explained by the flexibility of the UPEA chain: more methylene groups in the UPEA backbone resulted in higher flexibility.

The difference in $T_g$ ($\Delta T_g$=6° C.) between FPBe and FPB was attributed to their structural differences: FPBe has C═C double bonds in both the diester and diamide parts, but FPB has a C═C bond in the diamide part only. This difference in $T_g$ is much smaller than the difference between FPBe and APBe ($\Delta T_g$>40° C.). Therefore, the $T_g$'s of the synthesized UPEAs were effected more by the C═C bond located in the diamide block than by that located in the diester block. This may be attributed to the conjugation effect between the C═C double bonds and the carbonyl groups in the diamide part, which had a greater restriction on the bond rotation of the polymers.

Because of their unsaturated structure and the conjugation effect between the C═C double bond and the carbonyl groups, the fumaryl-based UPEAs (FPB, FPH, and FPBe) had much higher $T_m$'s than the corresponding saturated PEA reported previously. APBe and SPBe did not have $T_m$'s and decomposed when the temperature was greater than 240° C.; this means that they did not have a crystalline structure.

Solubilities determined for the UPEAs (50 mg samples) at room temperature (25° C.) in 10 solvents (1 mL) are set forth in Table 6 below:

TABLE 6

| | APBe | SPBe | FPB | FPH | FPBe |
|---|---|---|---|---|---|
| $H_2O$ | − | − | − | − | − |
| Formic Acid | + | + | − | − | ± |
| Trifluoroethanol | + | + | − | − | − |
| DMF | + | + | ± | ± | + |
| DMSO | + | + | + | ± | + |
| THF | + | + | − | − | − |
| Methanol | ± | − | − | − | − |
| Ethyl acetate | − | − | − | − | − |
| Chloroform | + | + | ± | − | − |
| Acetone | − | − | − | − | − |

[a]+ soluble; − insoluble; ± partially soluble or swelling.

As indicated by Table 6, all the UPEAs were completely or partially soluble in DMSO and DMF but could not dissolve in water, ethyl acetate, or acetone. UPEAs with a single unsaturated bond in each repeating diester unit (e.g., SPBe and APBe) could also dissolve in trifluoroethanol, formic acid, THF, and chloroform. Among the five UPEAs, the fumaryl-based ones (FPB, FPBe, and FPH) had poorer solubility, and FPH had the poorest solubility, probably because of not only the strong hydrogen bonds between the molecules (via the amide group) but also the conjugation effect between the C═C double bonds and carbonyl groups, which did not exist in APBe and SPBe. FPH had the longest —$CH_2$— chain in its diester part of the five UPEAs, and it resulted in the strongest intermolecular interaction, the highest hydrophobicity, and thus the poorest solubility. The higher solubility of FPB in formic acid and DMF and that of FPH in DMSO were obtained at a higher temperature (e.g., 70° C.).

Wide angle X-ray diffraction was carried out on the UPEAs. Fumaryl-based UPEAs FPH and FPB had well-defined semicrystalline structures, which explained why FPH and FPB had obvious melting peaks, whereas FPBe had a smaller peak; the other two UPEAs with unsaturated bonds in the diester segment (APBe and SPBe) did not have enough crystallinity and just decomposed when heated above approximately 240° C. SPBe existed almost in an amorphous state, and this explains why SPBe had the best solubility in some organic solvents, in comparison with the other UPEAs.

The polymers were obtained in fairly good yields at 70° C. in 48 h with DMA as the solvent. The molecular weights ($M_n$ and $M_w$) of SPBe and APBe, as measured by GPC, ranged from 10 to 30 kg/mol, and they had a rather narrow MWD of 1.40. The chemical structures of the UPEAs were confirmed by IR and NMR spectra. The UPEAs had higher $T_g$'s than saturated PEAs with similar backbone structures. The $T_g$'s of the synthesized polymers were affected more by the C═C double bond located in the diamide part than by that in the diester part. The solubility of the polymers was poor in water and better in DMA and DMSO.

WORKING EXAMPLE II

A working example of the second embodiment is provided by substituting p-toluenesulfonic acid salt of bis(L-phenylalanine) 2-butene-1,4-diester for (III) in Example 1 of U.S. Pat. No. 6,503,538 or by substituting di-p-nitrophenyl fumarate for (V) in Example 1 of U.S. Pat. No. 6,503,538 or by substituting p-toluenesulfonic acid salt of bis(L-phenylalanine) 2-butene-1,4-diester for (III) in Example 1 of U.S. Pat. No. 6,503,538 and also substituting di-p-nitrophenyl fumarate for (V) in Example 1 of U.S. Pat. No. 6,503,538.

VARIATIONS

The foregoing description of the invention has been presented describing certain operable and preferred embodiments. It is not intended that the invention should be so limited since variations and modifications thereof will be obvious to those skilled in the art, all of which are within the spirit and scope of the invention.

What is claimed is:

1. A polymer having the structural formula:

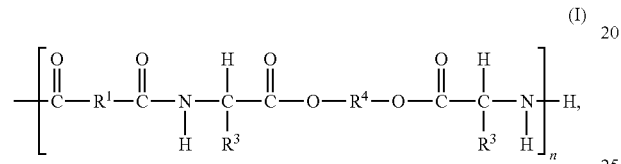

(I)

wherein $R_1$ is selected from the group consisting of ($C_2$-$C_{20}$) alkylene and ($C_2$-$C_{20}$) alkenylene; $R^3$ is selected from the group consisting of hydrogen, ($C_1$-$C_6$) alkyl, ($C_2$-$C_6$) alkenyl, ($C_2$-$C_6$) alkynyl and ($C_6$-$C_{10}$) aryl ($C_1$-$C_6$) alkyl; and $R^4$ is selected from the group consisting of ($C_2$-$C_{20}$) alkylene, ($C_2$-$C_{20}$) alkenylene, and (($CH_2$)$_r$O)$_q$-($C_2$-$C_{20}$) alkylene where r is 2 or 3 and q ranges from 1 to 4, and where at least one of $R^1$ and $R^4$ comprises a radical selected from the group consisting of ($C_2$-$C_{20}$) alkenylene; and n ranges from about 5 to about 150 attached via double bond functionality to non-biologic drug or bioactive agent selected from the group consisting of anti-inflammatory agents, antiproliferative agents, biologics, protein, cytokines, oligonucleotides, genes, carbohydrates and hormones.

2. A polymer having the structural formula:

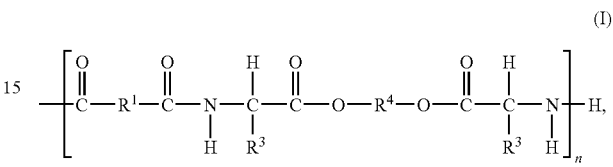

(I)

wherein $R^1$ is selected from the group consisting of ($C_2$-$C_{20}$) alkylene and ($C_2$-$C_{20}$) alkenylene; $R^3$ is selected from the group consisting of hydrogen, ($C_1$-$C_6$) alkyl, ($C_2$-$C_6$) alkenyl, ($C_2$-$C_6$) alkynyl and ($C_6$-$C_{10}$) aryl ($C_1$-$C_6$) alkyl; and $R^4$ is selected from the group consisting of ($C_2$-$C_{20}$) alkylene, ($C_2$-$C_{20}$) alkenylene, and (($CH_2$)$_r$O)$_q$-($C_2$-$C_{20}$) alkylene where r is 2 or 3 and q ranges from 1 to 4, and where at least one of $R^1$ and $R^4$ comprises a radical selected from the group consisting of ($C_2$-$C_{20}$) alkenylene; and n ranges from about 5 to about 150.

* * * * *